United States Patent [19] [11] 4,276,376
Hundt et al. [45] Jun. 30, 1981

[54] CREATINE KINASE CONTROL SERUM

[75] Inventors: Dieter Hundt, Percha; Marianne Sedelmeyer, Weilheim; Peter Röschlau, Seeshaupt; Fritz Stähler, Tutzing; Wolfgang Gruber, Tutzing-Unterzeismering, all of Fed. Rep. of Germany

[73] Assignee: Boehringer Mannheim GmbH, Mannheim, Fed. Rep. of Germany

[21] Appl. No.: 58,056

[22] Filed: Jul. 16, 1979

[30] Foreign Application Priority Data

Jul. 17, 1978 [DE] Fed. Rep. of Germany ....... 2831390

[51] Int. Cl.$^3$ .............................................. C12Q 1/50
[52] U.S. Cl. ..................................... 435/17; 435/188; 435/194
[58] Field of Search .......................... 435/17, 188, 194

[56] References Cited

U.S. PATENT DOCUMENTS 3,639,211  2/1972  Beaucamp ........................ 435/194 X

OTHER PUBLICATIONS

Von G. Szasz, Z. Klin. Chem. Klin. Biochem., vol. 8, pp. 212–217 (1970).
Chemical Abstracts, vol. 72, 108802p; 1970.

*Primary Examiner*—Robert J. Warden
*Attorney, Agent, or Firm*—Sprung, Felfe, Horn, Lynch & Kramer

[57] ABSTRACT

Control serum containing a defined content of creatine kinase comprising exogeneous creatine kinase in the form of swine serum and optionally additionally comprising human serum, other animal serum or serum albumin; and/or other enzyme substrates and metabolites occurring in serum.

9 Claims, No Drawings

CREATINE KINASE CONTROL SERUM

The invention relates to a control serum useful in clinical chemical analysis. More specifically, the invention is directed to a control serum containing creatine kinase of constant and specific activity.

The determination of creatine kinase (CK) plays an important part in clinical chemical analysis. For the control of such analyses it is necessary to provide for constant assurance of the correctness of the analysis with the aid of control serums having a known creatine kinase activity. Such control serums, when the creatine kinase is mainly based on human serum or bovine serum albumin, must be suitable for the control of the accuracy of the analysis of a number of different components. The control levels must be within a certain tolerance. This concept requires that the components in the control serum in the ready-to-use state, be stable for a given period of time, i.e., that their concentration or activity must not vary or at least not change substantially within this period of time. Considerable problems are encountered in achieving this stability when enzymes are components of such control serums.

In control sera which are commonly prepared on the basis of human serum, animal serum or bovine serum albumin, the CK activity must be increased by fortification, so as to assure ease of measurement and good precision. The term *fortification,* as used herein, refers to the addition of exogenous CK activity to the endogenous activity already present in the base material. The fortified CK activity, however, is not stable for sufficient time in the ready-to-use control serum, especially at room temperature, so that the maintenance of the level required in quality control is often problematical. A report is given in Z. Klin. Chem. Klin. Biochem. 8, 212-217 (1970), for example, on this extremely undesirable fault of creatine kinase of losing activity in the reconstituted control mixture. This rapid loss of activity, which can amount to as much as 40% within a few hours at room temperature, makes it necessary as a rule to use only freshly reconstituted control serum. This is not only difficult but also uneconomical.

The invention substantially overcomes or mitigates the above-mentioned disadvantages and provides a control serum of constant creatine kinase activity. The control serum of the invention is simple to use, does not require extensive laboratory skills and, importantly, is useable in the presence of other enzymes without affecting their activity and distorting the standard creatine kinase activity.

The invention essentially provides a control serum based on human serum, animal serum, or serum albumin having a certain enzyme content and also a content of any substrates, metabolites or other substances occurring in serum, and containing a certain amount of exogenous creatine kinase wherein swine serum is the exogenous creatine kinase.

It has formerly been common practice to use creatine kinase isolated from animal tissue and purified for the fortification of control serums. The invention is based upon the surprising discovery that, if whole swine serum is used instead of the formerly common purified tissue enzyme preparations, a surprisingly high and constant CK activity is sustained in the whole control serum. This effect cannot be achieved with purified CK from swine serum. The reason for this surprising property of swine serum is unknown. It is assumed, however, that the whole swine serum has a stabilizing effect on the CK, which is lost when the CK is isolated or purified.

It has formerly been common practice to fortify the control serum by adding isolated and purified CK from animal tissues, such as rabbit muscle for example. The swine serum used in accordance with the invention of itself has good endogenous CK activity is comparison with the endogenous CK activity of human serum. Therefore it is generally quite sufficient to add one part by volume of swine serum to fifty to a hundred and fifty parts by volume of the ready-to-use control serum medium, but greater and smaller amounts can also be used, such as one part to from twenty to one hundred and fifty parts by volume. These proportions relates to serum obtained by conventional methods. Swine serum in these amounts does not produce any disturbances in the control serum (in albumin electrophoresis for example). The invention is suitable for all common control serum media, such as solutions of human serum, bovine serum, horse serum and bovine serum albumin.

Control serums based on swine serum are known. On account of their high CK activity, however, they must be greatly diluted before use. This creates a serious source of error.

To prepare swine serum for use as "exogenous creatine kinase" in the control serum of the invention, it is sufficient to remove insoluble components, for example by filtration. No other preparatory steps are necessary. Since no purification of any kind is necessary, procedures such as have been required in the formerly known fortification with purified CK are unnecessary.

EXAMPLES

The following examples serve to further explain the invention.

EXAMPLE 1

The enzymes GOT, GPT, LDH, GlDH, ALD, LAP, alpha amylase, SP, AP, gamma-GT and lipase were added to 100 ml of human serum. Also, glucose, creatinine, urea, uric acid and bilirubin were added. The CK activity was adjusted to a desired level with the enzyme isolated from rabbit muscle and purified. The solution obtained was filtered clear and poured into vials in amounts of 5 ml each. After lyophilization, the samples were stored at +4° C. The change of activity found in the sample reconstituted with 5 ml of doubledistilled water and let stand at +25° C. is shown in the following table.

| 2 | 4 | 6 | 24 | (hours) |
|---|---|---|---|---|
| −21 | −28 | −31 | −47 | (%) |

EXAMPLE 2

The process of Example 1 is repeated, but the starting basis is 100 ml of 6% bovine serum albumin solution. The CK activity is again adjusted with enzyme isolated from rabbit muscle and purified. The activity change in the reconstituted sample when stored at +25° C. is shown in the following table:

| 2 | 4 | 6 | 24 | (hours) |
|---|---|---|---|---|
| −9 | −17 | −20 | −40 | (%) |

EXAMPLE 3

The procedure of Example 1 is repeated, but again 100 ml of human serum serves as the starting basis. The CK activity is adjusted by the addition of swine serum. Human serum+swine serum=100+1 (v+v). The following table shows the change of activity in the sample reconstituted and stored at +25° C.

| 2  | 4  | 6  | 24  | (hours) |
|----|----|----|-----|---------|
| −4 | −6 | −7 | −10 | (%)     |

EXAMPLE 4

The procedure of Example 1 is repeated, but 100 ml of 6% bovine serum albumin solution serves as the basis. The CK activity is adjusted by the addition of swine serum. Bovine serum albumin solution+swine serum=100+1 (v+v). The activity change in the sample reconstituted and stored at +25° C. is shown in the following table:

| 2  | 4  | 6  | 24 | (hours) |
|----|----|----|----|---------|
| +1 | −2 | −3 | −3 | (%)     |

EXAMPLE 5

The procedure of Example 1 is repeated, using 100 ml of bovine serum as the starting basis. The CK activity is adjusted by the addition of swine serum. Bovine serum+swine serm=100+1 (v+v). The activity change in the sample reconstituted and let stand at +25° C. is shown in the following table:

| 2  | 4  | 6  | 24 | (hours) |
|----|----|----|----|---------|
| −2 | −4 | −2 | −9 | (%)     |

EXAMPLE 6

The procedure of Example 1 is repeated, using 100 ml of horse serum as the starting basis. The CK activity is adjusted by the addition of swine serum. Horse serum+swine serum=100+1 (v+v). The activity change in the sample reconstituted and stored at +25° C. is shown in the following table:

| 2  | 4  | 6  | 24  | (hours) |
|----|----|----|-----|---------|
| −2 | −5 | −4 | −21 | (%)     |

It will be understood that the specification and examples are illustrative, but not limitative of the present invention and that other embodiments within the spirit and scope of the invention will suggest themselves to those skilled in the art.

What is claimed is:

1. Control serum comprising a base serum selected from the group consisting of human serum, animal serum or serum albumin and also containing a defined activity of creatine kinase, exogenous to said base serum, in the form of swine serum.
2. Control serum as claimed in claim 1 wherein said base serum is human serum.
3. Control serum as claimed in claim 1 wherein said base serum is bovine or horse serum.
4. Control serum as claimed is claim 1 wherein said base serum is serum albumin.
5. Control serum as claimed in claim 1 also comprising in said base serum other enzymes occurring in the serum.
6. Control serum as claimed in claim 1 also comprising in said base serum enzymes, substrates, and metabolites occurring in the serum.
7. Control serum as claimed in claim 1 comprising one volume part of swine serum contained in 50 to 150 volume parts of a medium for said conrol serum.
8. Control serum as claimed in claim 1 in lyophilized form.
9. Control serum as claimed in claim 8 wherein said control serum is reconstituted with an aqueous medium.